US012484890B2

(12) United States Patent
Ortiz Garcia et al.

(10) Patent No.: US 12,484,890 B2
(45) Date of Patent: Dec. 2, 2025

(54) TISSUE TRACTION DEVICES, SYSTEMS, AND METHODS, AND DEVICES, SYSTEMS, AND METHODS FOR DELIVERY THEREOF

(71) Applicant: BOSTON SCIENTIFIC SCIMED, INC., Maple Grove, MN (US)

(72) Inventors: Juan Pablo Ortiz Garcia, San Isidro (CR); Gary A. Jordan, Litchfield, NH (US); Barry Weitzner, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 381 days.

(21) Appl. No.: 18/107,222

(22) Filed: Feb. 8, 2023

(65) Prior Publication Data

US 2023/0248345 A1 Aug. 10, 2023

Related U.S. Application Data

(60) Provisional application No. 63/308,250, filed on Feb. 9, 2022.

(51) Int. Cl.
*A61B 17/02* (2006.01)

(52) U.S. Cl.
CPC .................................. *A61B 17/0218* (2013.01)

(58) Field of Classification Search
CPC .............. A61B 17/0218; A61B 17/083; A61B 2017/00269

(Continued)

(56) References Cited

U.S. PATENT DOCUMENTS 5,582,577 A * 12/1996 Lund .................. A61B 17/0218 600/233
2011/0021879 A1 1/2011 Hart et al.

(Continued)

FOREIGN PATENT DOCUMENTS

| | | |
|---|---|---|
| DE | 212019000166 U1 | 8/2020 |
| EP | 3689254 A1 | 8/2020 |
| JP | 2008142516 A | 6/2008 |

OTHER PUBLICATIONS

International Search Report and Written Opinion dated May 4, 2023 for International Application No. PCT/US2023/012600.

*Primary Examiner* — Eduardo C Robert
*Assistant Examiner* — Tara Rose E Carter
(74) *Attorney, Agent, or Firm* — Seager, Tufte & Wickhem, LLP

(57) ABSTRACT

A tissue traction device having more than one grasping segment by which the tissue traction device may be engaged with tissue directly, or indirectly, such as with the use of a tissue-engagement member. The tissue traction device may have a peripheral section defining grasping segments, as well as interior grasping segments defined within the perimeter of the peripheral section. Traction may be applied to a target tissue by engaging a target-tissue-engaging segment with target tissue, and engaging a traction-tissue-engaging segment with traction tissue spaced apart from the target tissue. Engagement of additional target-tissue-engaging segments with traction tissue (optionally at different locations) allows the force vector of the traction to be adjusted. A delivery system may include tissue traction device holder to maintain a desired configuration of the tissue traction device during delivery thereof to a target tissue area.

20 Claims, 4 Drawing Sheets

(58) Field of Classification Search
USPC .................................................. 600/201–245
See application file for complete search history.

(56) References Cited

U.S. PATENT DOCUMENTS

2021/0068805 A1* 3/2021 Ji ....................... A61B 17/0218
2021/0169464 A1 6/2021 Lee et al.

* cited by examiner

TISSUE TRACTION DEVICES, SYSTEMS, AND METHODS, AND DEVICES, SYSTEMS, AND METHODS FOR DELIVERY THEREOF

CROSS-REFERENCE TO RELATED APPLICATIONS

This application claims the benefit of priority of U.S. Provisional Application No. 63/308,250, filed Feb. 9, 2022, the entire disclosure of which is hereby incorporated by reference herein for all purposes.

FIELD

The present disclosure relates to the field of tissue traction devices, systems, and methods, and tissue traction delivery devices, systems, and methods.

BACKGROUND

Various surgical procedures involves lifting or separating target tissue (a designated section of tissue) at a treatment site, such as while the target tissue is still attached to the treatment site. A tissue traction element may be used to lift the target tissue away from the treatment site at which the procedure is being performed. In some instances, the target tissue is an unhealthy, diseased (i.e., cancerous, pre-cancerous etc.), or otherwise undesirable portion of tissue that may be healthy or unhealthy. A "target tissue" may also include tissues that are suspected of being unhealthy or diseased, but which require surgical removal for verification of their disease status by biopsy. Endoscopic Submucosal Dissection (ESD) and Endoscopic Mucosal Resection (EMR) are examples of outpatient procedures for removing deep tumors from the gastrointestinal (GI) tract. Even though this technique can allow patients to recover faster and often with less pain than with open or laparoscopic surgical procedures, such techniques require a high degree of expertise, and therefore are not yet widely adopted. One of the largest time and complexity drivers is managing the tissue being dissected/resected. As the medical professional cuts the tissue, it becomes harder to visualize the cutting plane (tissue to be cut) as tissue remains above the cutting plane, and also because the medical professional needs to cut continually deeper into the tissue. Accurately and efficiently performing an endoscopic tissue resection/dissection procedure includes the ability to maintain traction on the target tissue above the cutting plane as the boundaries of the target tissue are dissected and the tissue under traction is being lifted. Traction systems may be unable to maintain or adjust tension applied to the target tissue, possibly obstructing a medical professional's view of the target tissue and/or interfering with accessory tools. These complications may directly contribute to increased procedures time, complexity, and risk of perforation or bleeding. Additionally, traction devices may tend to fold or otherwise deform upon themselves during delivery, making the mere delivery of such device a challenge.

Improvements to not only tissue traction devices, systems, and methods, but also to devices, systems, and methods for delivering tissue traction devices would be welcome in the medical profession.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a tissue traction device has a peripheral section defining a perimeter of the tissue traction device and at least one grasping segment engageable with tissue, and at least one additional grasping segment extending within the perimeter of the peripheral section and engageable with tissue. In some embodiments, the grasping segments define at one target-tissue-engaging segment engageable with a target tissue, a first traction-tissue-engaging segment engageable with traction tissue spaced apart from the target tissue to apply traction to the target tissue, and a second traction-tissue-engaging segment engageable with traction tissue to vary the force vector of traction applied to the target tissue by the first traction-tissue-engaging segment.

In some embodiments, the distance between the second traction-tissue-engaging segment and the target tissue is shorter than the distance between the first traction-tissue-engaging segment and the target tissue. In some embodiments, the first traction-tissue-engaging segment and the second traction-tissue-engaging segment are engaged to traction tissue at the same location. In some embodiments, the first traction-tissue-engaging segment is engaged to traction tissue at a first location, and the second traction-tissue-engaging segment is engaged to traction tissue at a second location spaced apart from the first location.

In some embodiments, the first traction-tissue-engaging segment is engaged to traction tissue at a first location, and the second traction-tissue-engaging segment is engaged to traction tissue at a second location spaced apart from the first location to vary the force vector of traction applied to the target tissue.

In some embodiments, the first traction-tissue-engaging segment is defined along the peripheral section, and the at least one additional grasping segment defines the second traction-tissue-engaging segment within the perimeter of the peripheral section. In some embodiments, the peripheral section has an elliptical shape, the target-tissue-engaging segment is defined along a first focus of the elliptical peripheral section, the first traction-tissue-engaging segment is defined along a second focus of the elliptical peripheral section, and the grasping segment defining the second traction-tissue-engaging segment is a loop extending about the first focus of the elliptical peripheral section.

In some embodiments, the at least one additional grasping segment includes a first loop defining a first grasping segment and a second loop defining a second grasping segment within the perimeter of the peripheral section.

In some embodiments, the tissue traction device at least one of the additional grasping segments extends transverse to the direction in which the tissue traction device extends between the target tissue and the traction tissue.

In some embodiments, at least one of the grasping segments defined along the perimeter of the peripheral section or the at least one additional grasping segment extending within the perimeter of the peripheral section has a thickness different from another grasping segment of the tissue traction device.

In some embodiments, the tissue traction device is formed of an elastic material.

In accordance with various principles of the present disclosure, a delivery system for a tissue traction system includes a tissue traction device defining a peripheral section in the form of a loop defining at least one target-tissue-engaging segment and at least one traction-tissue-engaging segment spaced apart from the target-tissue-engaging segment; and a tissue traction device holder engageable with the tissue traction device to maintain the target-tissue-engaging segment spaced apart from the traction-tissue-engaging segment.

In some embodiments, the tissue traction device further includes at least one additional grasping segment defined along the peripheral section or extending within a perimeter defined by the peripheral section.

In some embodiments, the tissue traction system further includes a tissue-engagement member engaged with the target-tissue-engaging segment of the tissue traction device. In some embodiments, the delivery system further includes a tissue-engagement member delivery device extending within the tissue traction device holder and maintaining the tissue-engagement member and the target-tissue-engaging segment of the tissue traction device engaged therewith spaced apart from a portion of the tissue traction device engaged with the tissue traction device holder.

In accordance with various principles of the present disclosure, a method of applying traction to a target tissue includes engaging a target-tissue-engaging segment of a tissue traction device with target tissue; engaging a first traction-tissue-engaging segment of the tissue traction device with traction tissue spaced apart from the target tissue to apply traction to the target tissue, and engaging a second traction-tissue-engaging segment of the tissue traction device with traction tissue spaced apart from the target tissue to vary the force vector of the traction applied to the target tissue.

In some embodiments, the tissue traction device which is used includes a peripheral section defining a perimeter of the tissue traction device and at least one traction-tissue-engaging segment extending within the perimeter of the peripheral section, the method further including: engaging a target-tissue-engaging segment along the peripheral section of the tissue traction device with target tissue; engaging a first traction-tissue-engaging segment of the tissue traction device with traction tissue spaced apart from the target tissue to apply traction to the target tissue; and engaging a second traction-tissue-engaging segment of the tissue traction device extending within the perimeter of the peripheral section of the tissue traction device with traction tissue spaced apart from the target tissue to vary the force vector of the traction applied to the target tissue.

In some embodiments, the distance between the second traction-tissue-engaging segment and the target tissue is shorter than the distance between the first traction-tissue-engaging segment and the target tissue, and the method further includes engaging the first traction-tissue-engaging segment and the second traction-tissue-engaging segment to traction tissue at the same location.

In some embodiments, engaging the second traction-tissue-engaging segment to traction tissue includes engaging the second traction-tissue-engaging segment to traction tissue spaced apart from traction tissue to which the first traction-tissue-engaging segment is engaged.

In some embodiments, the method further includes delivering the tissue traction device to the target tissue with a tissue traction device holder maintaining the target-tissue-engaging segment of the tissue traction device apart from the first traction-tissue-engaging segment of the tissue traction device.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements among embodiments are typically represented by the same reference characters, and similar elements are typically designated with similar reference numbers differing in increments of 1000, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
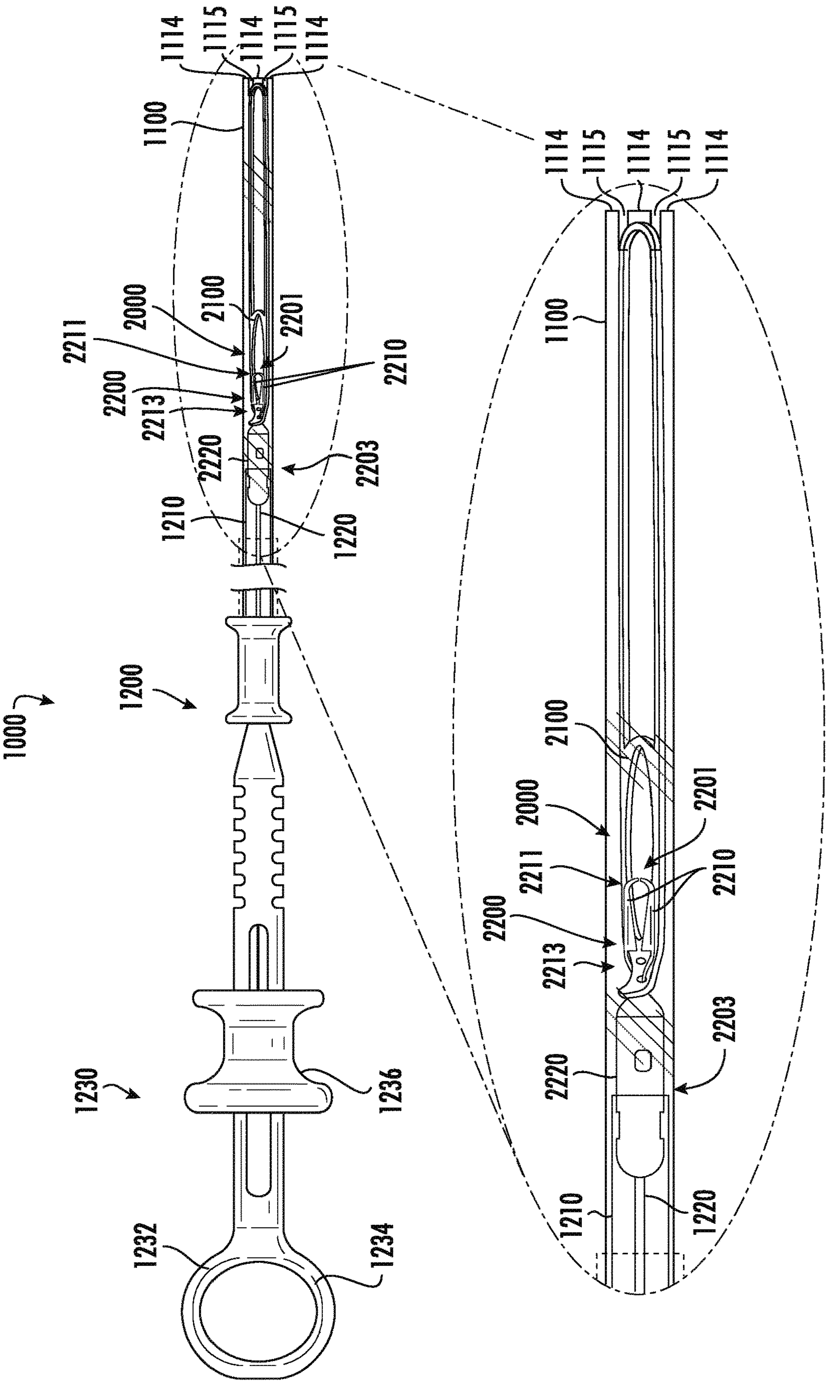
FIG. 1 illustrates an elevational view of an example of an embodiment of a traction device and system, and an associated delivery device and system, formed in accordance with various aspects of the present disclosure, including a detail view of a portion thereof.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, “proximal” refers to the direction or location closest to the user (medical professional or clinician or technician or operator or physician, etc., such terms being used interchangeably herein without intent to limit, and including automated controller systems or otherwise), etc., such as when using a device (e.g., introducing the device into a patient, or during implantation, positioning, or delivery), and/or closest to a delivery device, and “distal” refers to the direction or location furthest from the user, such as when using the device (e.g., introducing the device into a patient, or during implantation, positioning, or delivery), and/or closest to a delivery device. “Longitudinal” means extending along the longer or larger dimension of an element. “Central” means at least generally bisecting a center point and/or generally equidistant from a periphery or boundary, and a “central axis” means, with respect to an opening, a line that at least generally bisects a center point of the opening, extending longitudinally along the length of the opening when the opening comprises, for example, a tubular element, a channel, a cavity, or a bore. As used herein, a “free end” of an element is a terminal end at which such element does not extend beyond.

The present disclosure relates to a variety of devices, systems, and methods for applying traction to tissue within a body. A number of medical procedures, including those performed along the digestive and/or biliary tract, utilize medical devices to access tissue intended for removal (e.g., “target tissue”) within the body. For example, in some current medical procedures (e.g., endoscopic submucosal dissection (ESD), endoscopic mucosal resection (EMR), Peroral Endoscopic Myotomy (POEM), cholecystectomy, Video-Assisted Thoracoscopic Surgery (VATS)), medical professionals may utilize an endoscope or similar medical device during access and removal of diseased lesions. The endoscope may be capable of both accessing the target tissue site (the site at which the target tissue is located) while also permitting various tissue manipulating devices to be deployed therethrough. Such tissue manipulating devices include, without limitation, devices for resecting target tissue, which include, without limitation, cutting devices such as knives, scalpels, scissors, electrocauterization devices, end effectors, graspers, snares, forceps, dissectors, energy-based tissue coagulators or cutters, clamps, tissue staplers, tissue loops, clip appliers, suture delivering instruments, etc., the particular device not being critical to the present disclosure. It will be appreciated that terms such as medical tools, instruments, devices, etc., may be used interchangeably herein without intent to limit. Additionally, in some instances, an endoscope may incorporate features which assist the medical professional in visualizing and/or imaging the tissue dissection/resection procedure, such as to facilitate performance of the procedure. For example, some endoscopes may include a light and/or camera designed to illuminate and/or visualize the treatment site/target tissue area as the endoscope is navigated and positioned adjacent to the target tissue site. Additionally, some endoscopes may also include a lumen (e.g., a working channel) through which a further instrument, and optionally also a delivery sheath for the instrument, may be deployed and utilized. Additional visualization methods (e.g., fluoroscopy) may be alternatively or additionally employed. It will be appreciated that reference is made herein to tissue resection (and other grammatical forms thereof) for the sake of convenience, such term encompassing tissue dissection, cutting, manipulation, etc. (and other grammatical forms thereof) without intent to limit.

While physicians are becoming more proficient at resecting diseased lesions from within the body (e.g., within the digestive tract, abdominal cavity, thoracic cavity, etc.), present traction methods may continue to be inefficient to the physician. For example, in some instances poor visualization and poor ability to engage and manipulate tissue may result in a prolonged tissue dissection procedure. It may be desirable to lift or to retract the tissue out of the field of vision or out of the way of the instrument being used to perform the procedure. For instance, in some EMR/ESD procedures, physicians may use separate devices to provide a means of tissue traction, such as to move tissue with respect to surrounding tissue. Positioning and maneuvering (e.g., traction) of a resected tissue flap during and after resecting presents various challenges. Such procedures may include multiple device manipulations and/or exchanges, and accompanying extended procedure times. Such systems may be unable to maintain or adjust traction or tension applied to the target tissue, and/or may maintain or adjust traction or tension applied to the target tissue in an inefficient or inconsistent manner.

In accordance with various principles of the present disclosure, a tissue traction device is used to apply traction to tissue to facilitate performance of a procedure with respect to such tissue. The tissue traction device (which may be alternately referenced herein as a tether for the sake of convenience and without intent to limit) may be a traction band, elastic band, stretchable elongate member, wire, cord, cable, spring, suture, and/or any other suitable member, which optionally is stretchable and/or elongatable. It will be appreciated that the tether may advantageously be elastic and/or elastomeric (e.g., formed of rubber), though elasticity and/or stretchability are not necessarily aspects of a traction device formed in accordance with various principles of the present disclosure and/or used with a delivery device and system configured to deliver a tissue traction device to a deployment site. The tissue traction device is engaged with tissue either directly or indirectly (e.g., via another element, such as a tissue-engagement member). It will be appreciated that terms such as engage (and other grammatical forms thereof) may be used interchangeably herein with terms such as couple, grasp, hold, clasp, clip, anchor, attach, affix, secure, etc. (and other grammatical forms thereof), without intent to limit.

A tissue-engagement member used in accordance with various principles of the present disclosure may alternately be referenced herein as a tissue fastener or clip or other mechanical securing device (e.g., a hemostatic clip, clamp, grasper, basket, gripper, magnet, adhesive, etc.), without intent to limit. The tissue-engagement member is optionally separately formed from the tissue traction device. In some embodiments, the tissue-engagement member is repositionable after being partially deployed. For example, the tissue-engagement member may be configured to allow for the tissue-engagement member to be releasably engaged (e.g., closed, but not locked, into engagement) with tissue when in a first configuration, and locked against opening out of engagement with tissue when in a second closed configuration. In some embodiments, the tissue-engagement member has grasper arms or jaws selectively movable away from each other to engage tissue therebetween, and movable towards each other to grasp the engaged tissue. The grasper arms may be hinged together (e.g., as a single piece), or separately formed and movable with respect to each other, such as by being pivotable about a pivot point. The grasper arms may have one or more additional grasping feature, such as a sawtooth or crenulated profile or teeth, at ends and/or along edges of the grasper arms. In some embodiments, the tissue-engagement member is movable with respect to the tissue traction device, even when coupled thereto. Movement, such as rotation (e.g., 3600 rotation), of the tissue-engagement member may be controlled by a proximal control knob, dongle, or other actuator element. In some embodiments, the tissue-engagement member may be maneuvered, e.g., rotated, with one-to-one correspondence between movement of a control knob and the tissue-engagement member. In some embodiments, the tissue-engagement member is releasable from the delivery device used to deliver the tissue-engagement member. For instance, a frangible connection between the tissue-engagement member and the delivery device may be overcome and/or a threshold pressure may be exerted to separate a jointed (e.g., ball and yoke) connection. It will be appreciated that the present disclosure is not to be limited to a particular form or configuration of a tissue-engagement member.

Tissue traction devices known in the medical industry, as well as embodiments disclosed herein, may be difficult to deliver to the target tissue site. For instance, some tissue traction devices are flexible and may fold or wrap upon themselves, collapse, crumple, wrinkle, bend, ball up, bunch up, deform, distort, etc., (which may interfere with or hinder delivery of the tissue traction device, such as by increasing the profile of the tissue traction device within a narrow delivery channel) and/or may become entangled with a tissue-engagement member with which the tissue traction device is engaged with tissue at the target tissue site. For the sake of convenience, and without intent to limit, reference is made to distortion of the tissue traction device (or other grammatical forms of the term distortion) and/or maintaining the tissue traction device in a generally elongated configuration. It will be appreciated that reference to "generally elongated" does not necessarily require a precisely straight configuration, but, rather, a configuration which allows ready use of the tissue traction device upon delivery to the target tissue site as may be appreciated by one of ordinary skill in the art. Alternatively or additionally, a generally elongated configuration of a tissue traction device generally reduces the profile of the tissue traction device as it is delivered to, e.g., the target tissue site, such as through the narrow lumen of an endoscope. It will be appreciated that reference to "at" the target tissue site is intended to include tissue at and about the vicinity of the target tissue, and is not limited to just target tissue. Delivery of a tissue traction device may be further complicated if the tissue traction device is elastic and/or has other properties tending to interfere with elongating the tissue-engagement member once folded on itself or otherwise no longer elongated.

In accordance with various principles of the present disclosure, a tissue traction device is delivered to a target tissue site with the assistance of a tissue traction device holder configured to maintain the tissue traction device in a configuration facilitating use thereof at the target tissue site in a manner appreciated by those of ordinary skill in the art. More particularly, the tissue traction device holder may be configured and/or positioned with respect to a delivery device and a delivery system to hold a target-tissue-engaging segment of a tissue traction device spaced apart from a traction-tissue-engaging segment of a tissue traction device so that such segments may be readily engaged respectively with target tissue and traction tissue upon delivery to a target tissue site (e.g., without manipulation of the tissue traction device such as from an entangled or folded configuration). In some embodiments, a tissue traction device is in a generally elongated configuration during delivery so that the tissue traction device does not bunch up or collapse or otherwise deform in a manner which may interfere with delivery to and use with respect to the target tissue. In some embodiments, at least a portion of the tissue traction device is mounted with respect to, or otherwise operatively coupled with the tissue traction device holder in an elongated configuration.

A delivery device used herewith may be any suitable size, cross-sectional shape or area, and/or configuration permitting introduction and passage of medical instruments to a target tissue site/treatment site (such terms may be used interchangeably herein without intent to limit). It is generally beneficial for the delivery device to be steerable, and the delivery device may have different areas of different flexibility or stiffness to promote steerability. The delivery device may be in the form of a flexible elongate tubular member and may include one or more working channels or lumens extending substantially longitudinally (axially)

between the proximal end and the distal end of the delivery device. It will be appreciated that the term flexible elongate tubular member is used herein for the sake of convenience as an example of a delivery device in general and without intent to limit, and may be in the form of a catheter, sheath, tube, cannula, etc. (such terms being used interchangeably herein without intent to limit) or other configuration of an introducer. The delivery devices and/or overtubes associated therewith may be made from any suitable biocompatible material known to one of ordinary skill in the art and having sufficient flexibility to traverse non-straight or tortuous anatomy. Such materials include, but are not limited to, rubber, silicon, synthetic plastic, stainless steel, metal-polymer composite; metal alloys of nickel, titanium, copper cobalt, vanadium, chromium, and iron; superelastic or shape memory material such as nitinol (nickel-titanium alloy); different layers of different materials and reinforcements. Such materials may be made of or coated with a polymeric or lubricious material to enable or facilitate passage of the delivery device through a body and/or passage of additional instruments through working channels extending therethrough.

In accordance with various principles of the present disclosure, a tissue traction device delivery system is configured to navigate through body passages (e.g., through the gastrointestinal system, such as via mouth or nose and through the esophagus and stomach) to deliver a tissue traction device through the body to the target tissue site. In some embodiments, a tissue traction device delivery system includes one or more delivery devices. The delivery devices may include one or more flexible elongate tubular members. In some embodiments, the one or more flexible elongate tubular members include an endoscope with a working channel through which a tissue traction system, including the tissue traction device and, optionally, one or more tissue-engagement members, is delivered. In some embodiments, the tissue traction device holder is a flexible elongate tubular member within and along which the tissue traction device is delivered. In some embodiments, a tissue-engagement member is delivered at, adjacent, along, etc., the end of a flexible elongate control member operatively engaged with the tissue-engagement member to control movement thereof (advancement, withdrawal, rotation, actuation such as opening and closing to grasp tissue, etc.), such as via a control handle at a proximal end of the flexible elongate control member. It will be appreciated that the term control (and other grammatical forms thereof) may be used interchangeably herein with terms such as manipulate, move, maneuver, actuate, navigate, etc., (including other grammatical forms thereof) without intent to limit. In some embodiments, the tissue-engagement member and the flexible elongate control member are delivered with a flexible elongate tubular member movably (e.g., axially and/or rotationally) extending within the tissue traction device holder. In embodiments in which an end of a tissue traction device is coupled with a tissue-engagement member, the tissue traction device may extend, within or along the tissue traction device holder, distally from the tissue-engagement member to be operatively coupled with the tissue traction device holder at another end or location along the tissue traction device.

In some embodiments, the tissue traction device is delivered to the target tissue site with a tissue-engagement member coupled thereto. In some embodiments, the tissue traction device extends from a tissue-engagement member to the tissue traction device holder. For instance, the tissue-engagement member may be coupled with a first end of a tissue traction device, and the second end of the tissue traction device may be operatively engaged with the tissue traction device holder (such as at a position spaced apart from the tissue-engagement member) to prevent the tissue traction device from being distorted. It will be appreciated that reference to a first end or a second end of the tissue traction device is for the sake of simplicity, and is not to be understood as being limited to an end of an elongated element, but may also apply to other locations along an elongated element. By extending the tissue traction device from the tissue-engagement member to the tissue traction device holder, the tissue traction device is maintained in a generally elongated configuration which facilitates delivery and deployment thereof (e.g., during introduction and movement through a delivery device such as a flexible tubular element) and attachment to tissue at the target tissue site. In some embodiments, the tissue traction device holder is extended distally beyond the delivery device, such as distal to the tissue-engagement member, thereby keeping the tissue traction device extended during delivery. Such configuration, which may be considered a “slingshot” configuration, may provide an advantage over back-loaded devices which may be more time consuming to assemble for delivery of a tissue traction device to the target tissue site.

Once the tissue traction device is delivered to the target tissue site, a first section of the tissue traction device is engaged with tissue at the target tissue site, such as with the use of an initial or first tissue-engagement member (optionally pre-loaded or otherwise coupled to the tissue traction device prior to delivery to the target tissue site). For the sake of convenience, and without intent to limit, the tissue which is initially engaged by the tissue traction device is referenced herein as the target tissue, although tissue other than the target tissue may be initially engaged instead. A traction section of the tissue traction device is then engaged with tissue spaced apart from the target tissue (referenced herein as an initial traction tissue site without intent to limit), such as in a manner which allows the tissue traction device to apply traction to the target tissue. A second tissue-engagement member may be used to engage the traction section of the tissue traction device with the traction tissue site. As the target tissue is moved with respect to the surrounding tissue (e.g., cut with respect to surrounding tissue), the traction applied thereto may decrease. In accordance with various principles of the present disclosure, rather than moving the traction section of the tissue traction device to increase tension on the target tissue, another/additional traction section is engaged with tissue at another/additional traction tissue site spaced apart from the initial traction tissue site to increase the traction applied to the target tissue site. A third tissue-engagement member may be used to engage the additional traction section of the tissue traction device with the additional traction tissue site. Additional traction sections of the tissue traction device may be engaged with additional traction tissue sites, such as increasingly further from the target tissue.

In accordance with various principles of the present disclosure, a tissue traction device is shaped to allow different points of attachment of the tissue traction device to tissue, such as with the use of a tissue-engagement member. For instance, in some embodiments, a tissue traction device formed in accordance with various principles of the present disclosure has more than one grasping section or segment distinct from another grasping section or segment. It will be appreciated that terms such as section or segment or area or portion or the like may be used interchangeably herein without intent to limit. For the sake of convenience in differentiation, different sections of the tissue traction device may be distinguished from one another by referring to different grasping "segments" defined along a section of the tissue traction device such as by a difference in shape or orientation with respect to another grasping segment of the tissue traction device (such as, without limitation, adjacent or adjoining the grasping segments). In one aspect, a tissue traction device may be formed in accordance with various principles of the present disclosure with an outer or peripheral section defining one or more grasping segments therealong, and one or more grasping segments within the interior region or periphery of the peripheral section. A target-tissue-engaging segment may be identified (e.g., along a portion of the peripheral section of the tissue traction device, or optionally along a section within the perimeter of the peripheral section) as a portion which is attached to the target tissue to which traction is to be applied. Additional grasping segments may be defined along the peripheral section of the tissue traction device, and/or by sections of the tissue traction device within the perimeter of the peripheral section of the tissue traction device. One or more additional grasping segments may be engaged with traction tissue sites (the same or different site as the initially engaged traction tissue), such grasping segments being referenced herein as traction-tissue-engaging segments for the sake of convenience (such as to differentiate from target-tissue-engaging segments) and without intent to limit. A tissue traction device formed in accordance with various principles of the present disclosure thus provides a plurality of grasping segments or holding places for the medical professional to grasp to maneuver the tissue traction device and/or to engage the tissue traction device with a selected region of tissue along the tissue target site (e.g., the target tissue or traction tissue), thereby improving the usability of the tissue traction device.

In some embodiments, the peripheral section of a tissue traction device formed in accordance with various principles of the present disclosure is in the shape of a loop. In some embodiments, the loop is in the shape of an ellipse. In some embodiments, one or more additional sections, such as in the form of additional loops, are formed within the peripheral section. For instance, in some embodiments, a loop (such as a circle) may be formed along one or both of the foci of an outer peripheral section in the form of an ellipse. In some embodiments, the additional sections are formed by other segments (straight or curved) extending within the peripheral section, such as extending transversely across the peripheral section (e.g., transverse to a direction of elongation of the peripheral section in a direction between the target tissue and the traction tissue).

A tissue traction device formed in accordance with various principles of the present disclosure provides the medical professional with multiple points at which the tissue traction device may be coupled to tissue spaced away from the target tissue (such as with one or more tissue-engagement members) to vary or adjust the force vector applied to the target tissue to apply traction thereto. For instance, engaging a first segment of the tissue traction device to a first region of tissue (such as, without limitation, target tissue), and then engaging (sequentially or at the same time) different segments of the tissue traction device to different regions of tissue spaced apart from the first region of tissue allows varying degrees or intensities and/or varying angles of traction to be applied to the target tissue. If the medical professional engages a first segment of the tissue traction device to a first tissue site, and a second segment of the tissue traction device to a second tissue site, and then needs to adjust the traction on the first tissue site (e.g., to apply additional, greater traction to the first tissue site, or traction at a different angle), a third segment of the tissue traction device may be engaged with a third tissue site to apply a greater amount of traction to the first tissue site (such as if the distance between the third segment and the first segment is shorter than the distance between the second segment and the first segment) and/or to vary the angle at which traction is applied to the first tissue site. It will be appreciated that the second and third tissue sites may be considered traction tissue sites. It will further be appreciated that the second and third segments of the tissue traction device may be different lengths such that engagement of such segments to the same traction tissue site applies traction with different force vectors to the target tissue. In some embodiments, the tissue traction device is made of an elastomeric material that will apply a traction force to the tissue to which it is engaged, such as when placed correctly. In some embodiments, the tissue traction device is elastic. In some embodiments, the tissue traction device is elongatable to apply traction to tissue at the target tissue site.

Various embodiments of tissue traction devices and systems, and associated methods, as well as tissue traction delivery devices and systems, and associated methods will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present disclosure is not limited to only the embodiments specifically described herein, and the examples of embodiments disclosed herein are not intended as limiting the broader aspects of the present disclosure.

Turning now to the drawings, it will be appreciated that common features are identified by common reference elements and, for the sake of brevity and convenience, and without intent to limit, the descriptions of the common features are generally not repeated. For purposes of clarity, not all components having the same reference number are numbered. It will be appreciated that, in the following description, elements or components similar among the various illustrated embodiments of tissue-engagement members are generally designated with the same reference numbers increased by a multiple of 1000 and redundant description is generally omitted for the sake of brevity. Moreover, certain features in one embodiment of a tissue-engagement member may be used across different embodiments of tissue-engagement members and are not necessarily individually labeled when appearing in different embodiments.

Figure 10:
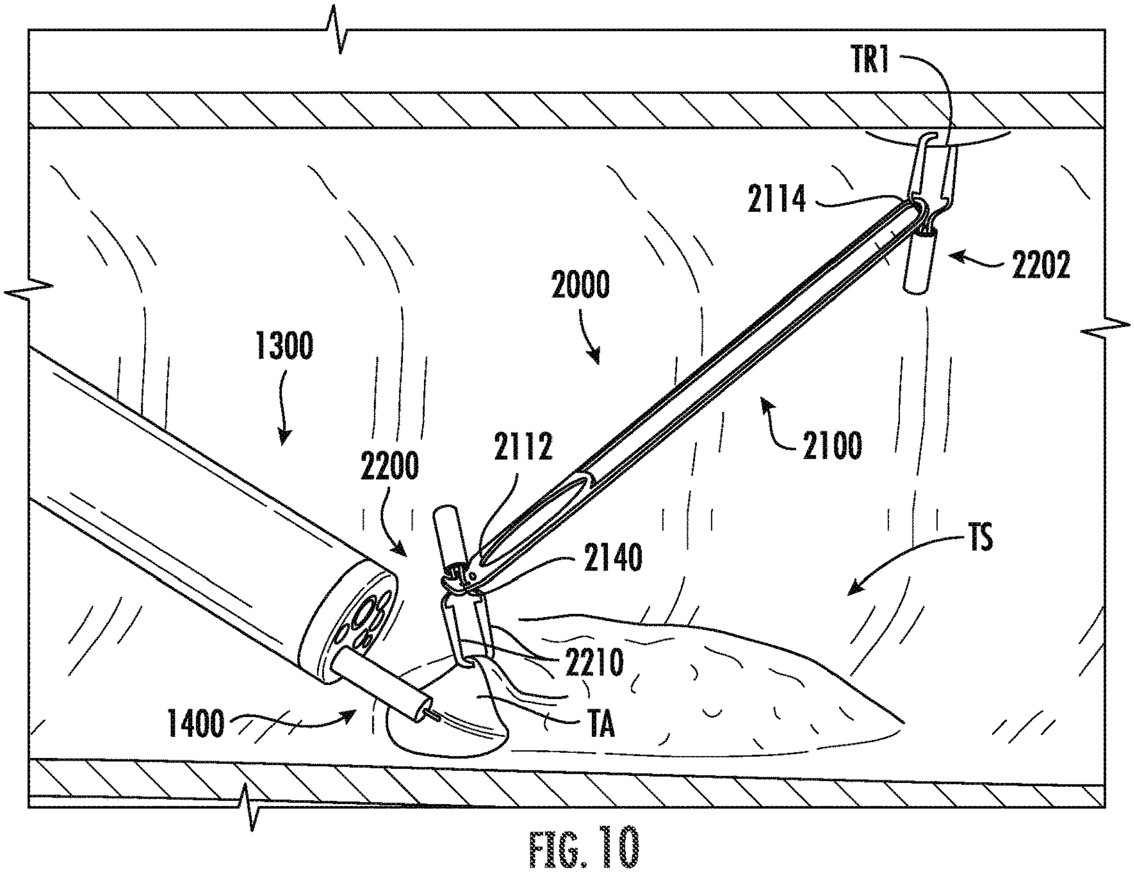
FIG. 10 illustrates an example of an environment in which devices, systems, and methods in accordance with various principles of the present disclosure may be used, with an example of an embodiment of a traction device and system being implemented.
Figure 11:
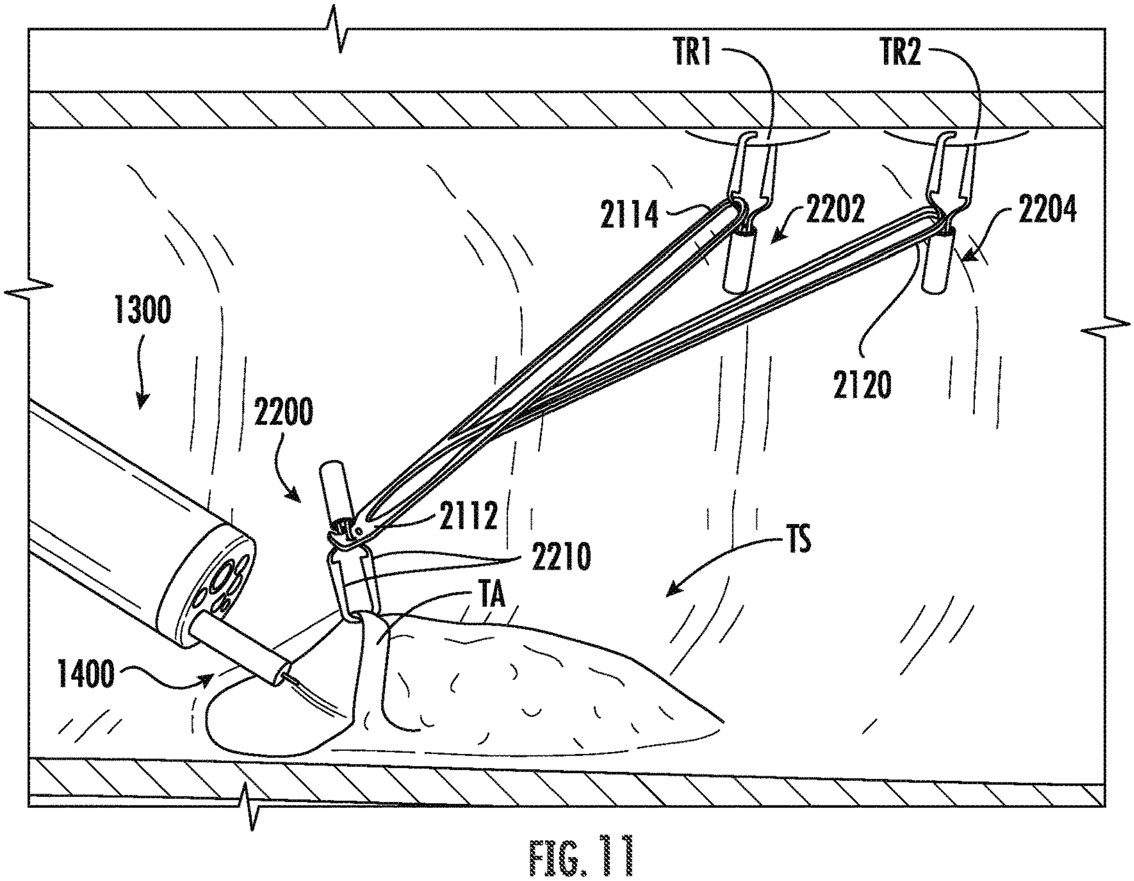
FIG. 11 illustrates an example of an environment as in FIG. 10, with an example of an embodiment of a traction device and system as in FIG. 10 being further implemented.

An example of an embodiment of a delivery system 1000 formed in accordance with various principles of the present disclosure to deliver a tissue traction system 2000 is illustrated in FIG. 1. The tissue traction system 2000 includes a tissue traction device 2100, and a tissue-engagement member 2200 with which the tissue traction device 2100 may be engaged with tissue at a target tissue site. The delivery system 1000 includes a tissue traction device holder 1100 configured to maintain the tissue traction device 2100 in a delivery configuration, and a tissue-engagement member delivery device 1200 configured to deliver the tissue-engagement member 2200. In the illustrated example of an embodiment, the tissue-engagement member delivery device 1200 includes a flexible elongate tubular member 1210 with which the tissue-engagement member 2200 is delivered. The flexible elongate tubular member 1210 is referenced herein as a tissue-engagement member shaft 1210 for the sake of clarity and without intent to limit. In some embodiments, a distal end 1211 of the tissue-engagement member shaft 1210 is operatively coupled with a proximal end 2203 of the tissue-engagement member 2200, and the distal end 2201 of the tissue-engagement member 2200 is operatively coupled with a proximal end 2203 the tissue-engagement member 2200. The tissue-engagement member 2200 may be delivered within a lumen defined within the tissue-engagement member shaft 1210, or at least a portion of the tissue-engagement member 2200 may extend distally outside the tissue-engagement member shaft 1210. If the latter, then the tissue traction device holder 1100 may extend over the tissue-engagement member shaft 1210 and the tissue-engagement member 2200 and may shield the tissue-engagement member 2200 (particularly the grasper arms 2210 thereof) from the interior of another flexible elongate tubular member in which the tissue-engagement member delivery device 1200 is delivered. For instance, the tissue traction device holder 1110 may be in the form of a flexible elongate tubular member extending over the tissue-engagement member shaft 1210. The tissue traction device holder 1100 and the tissue-engagement member shaft 1210 may be delivered within another delivery member, such as another flexible elongate tubular member, such as known to those of ordinary skill in the art. For instance, the tissue traction device holder 1100 and the tissue-engagement member shaft 1210 may be delivered within a working channel of an endoscope 1300 (such as known to those of ordinary skill in the art, the configuration of which does not form a part of the present disclosure), such as illustrated in FIG. 10 and FIG. 11, as discussed in further detail below, and/or within a further delivery shaft (such as in the form of a flexible elongate tubular member).

As may be appreciated with reference to FIG. 1, a portion of the tissue traction device 2100 may be coupled to the tissue-engagement member 2200. The tissue-engagement member 2200 may be engaged with tissue at the target tissue site and the portion of the tissue traction device 2100 coupled thereto may thereby be coupled to tissue at the target tissue site as well. Another portion of the tissue traction device 2100, spaced apart from the portion engaged with the tissue-engagement member 2200, engages a portion of the tissue traction device holder 1100 to be held by the tissue traction device holder 1100 in a configuration which facilitates delivery of the tissue traction device 2100 to the target tissue site. For instance, the tissue traction device holder 1100 may hold the tissue traction device 2100 in a configuration (such as a generally elongated configuration) which facilitates deployment of the tissue traction device 2100. In the illustrated embodiment, the tissue traction device 2100 is extended distally so that an anchoring portion (spaced apart from the tissue-engaging portion) of the tissue traction device 2100 engages a portion of the tissue traction device holder 1100, such as a distal end 1101 of the tissue traction device holder 1100. As such, the section of the tissue traction device 2100 to be engaged with traction tissue may be maintained spaced apart from the section of the tissue traction device 2100 to be engaged with target tissue. However, other configurations and/or arrangements of the tissue traction device 2100 with respect to the tissue traction device holder 1100 are within the scope and spirit of the present disclosure.

In some embodiments, the tissue traction device holder 1100 is sized, shaped, configured, and/or dimensioned for engagement with (e.g., operative coupling with) a portion of the tissue traction device 2100 to hold the tissue traction device 2100 in place with respect to the tissue traction device holder 1100. Such structure, referenced herein as a coupler 1110 for the sake of convenience, may be a shoulder, cutout section, post, rail, slat, projection, hook, ledge, or other structure known to those of ordinary skill in the art as couplers. In the example of an embodiment illustrated in FIG. 1, the coupler 110 is in the form of two or more slits 1115 defining therebetween a rail 1114 in the distal end 1101 of the tissue traction device holder 1100. A portion of the tissue traction device 2100 may be inserted in one or both slit 1115. For instance, a tissue traction device 2100 with at least a portion thereof in the form of a loop may be hooked about a rail 1114 defined by slits 1115. It will be appreciated that configurations of a coupler 1110 other than the configuration illustrated in FIG. 1 are within the scope and spirit of the present disclosure.

In some embodiments, the tissue-engagement member 2200 is an adjustable clip (such as a hemostatic clip) with first and second grasper arms 2210 (which may be alternately referenced herein as jaws without intent to limit) movable with respect to each other between an open configuration and a closed configuration. In the open configuration, tissue may be positioned between the grasper arms 2210 to be engaged by the grasper arms 2210. In the closed configuration, the grasper arms 2210 engage or hold tissue therebetween. The grasper arms 2210 may be delivered by the tissue-engagement member delivery device 1200 in a closed configuration which generally is more compact than the open configuration, although the present disclosure need not be so limited. The tissue-engagement member 2200 may be configured to be engaged with tissue at the target tissue site TS (such as illustrated in FIG. 10 and FIG. 11 and discussed in further detail below), as well as to be engaged with the tissue-engaging portion of the tissue traction device 2100. As such, the tissue-engaging portion of the tissue traction device 2100 need not engage tissue directly, but may be engaged with tissue at the target tissue site via the tissue-engagement member 2200.

In some embodiments, the tissue-engagement member delivery device 1200 includes a tissue-engagement member controller 1210 engaged with the tissue-engagement member 2200 (e.g., a proximal end 2203 of the tissue-engagement member 2200) to control movement of the grasper arms 2210 relative to each other. In some embodiments, the tissue-engagement member 2200 is slidable within a capsule 2220 (a tubular element with a lumen defined therein), and the grasper arms 2210 may be biased apart such that when the grasper arms 2210 are extended distally outside the capsule 2220 the grasper arms 2210 are in an open configuration. The grasper arms 2210 may be configured to shift to a closed configuration when withdrawn at least partially within the capsule 2220, generally leaving the distal ends 2211 thereof outside the capsule 2220 (such as when engaging tissue, so that the tissue is not extended into the capsule 2220). The controller 1210 may be a flexible elongated member, such as a control wire, capable of extending proximally from the tissue-engagement member 2200 to a proximal location outside the body at which the controller 1210 may be manipulated to move (e.g., to axially translate, to rotate, etc.) the tissue-engagement member 2200. For instance, distal advancement of the controller 1210 advances the tissue-engagement member 2200 out of the capsule 2220 to allow the grasper arms 2210 to move to an open configuration to allow tissue to positioned therebetween, and proximal retraction of the controller 1210 retracts the tissue-engagement member 2200 into the capsule 2220 to shift the grasper arms 2210 into a closed configuration grasping tissue therebetween. Various structures and features such as known to those of ordinary skill in the art may be provided, such as known to those of ordinary skill in the art, to prevent the grasper arms 2210 from being pushed out of the capsule 2220 and/or to inhibit the grasper arms 2210 from being withdrawn too far into the capsule 2220 (e.g., pulling the grasped tissue therein), the present disclosure not being limited by such structures or features. Moreover, any of a variety of locking features, such as known to those of ordinary skill in the art, may be provided to hold the grasper arms 2210 in a desired open or closed configuration, the present disclosure not being limited by such structures or features Once the grasper arms 2210 of the tissue-engagement member 2200 are engaged in a desired manner with tissue, and/or are in a desired configuration, the controller 1210 may be decoupled (e.g., broken away) from the tissue-engagement member 2200 to leave the tissue-engagement member 2200 in place engaging tissue as desired. Any of a variety of configurations and methods of decoupling such components known or heretofore known in the art may be used without impacting the scope of the present disclosure.

In the example of an embodiment of a delivery system 1000 illustrated in FIG. 1, delivery and deployment of the tissue traction device 2100 and the tissue-engagement member 2200 at the distal end 1001 of the delivery system 1000 is controlled or actuated by a control handle 1230 at a proximal end 1003 of the delivery system 1000. The illustrated example of an embodiment of a control handle 1230 includes a handle body 1232 graspable by a medical professional, and optionally including a thumb ring 1234. The illustrated example of an embodiment of a control handle 1230 also includes a slider 1236 coupled to the controller 1210 to effectuate movement of the controller 1210 and thus movement of the tissue-engagement member 2200. For instance, the slider 1236 may be slidable with respect to the control handle 1230 to advance or retract the controller 1210 and thus the grasper arms 2210 with respect to the capsule 2220 to shift the grasper arms 2210 between open and closed configurations. It will be appreciated that various configurations of control handles and manners of delivering a tissue traction device 2100 formed in accordance with various principles of the present disclosure, optionally with a tissue traction device holder 1100 formed in accordance with various principles of the present disclosure, are within the scope of the present disclosure, the particular configurations not being critical to the present disclosure.

In accordance with various principles of the present disclosure, any of a variety of tissue traction devices may be delivered by a delivery system 1000 utilizing a tissue traction device holder 1100 such as illustrated in FIG. 1. In some embodiments, the tissue traction device 2100 includes more than one area or portion or section engageable with another element such as tissue, a tissue-engagement member 2200, or a tissue traction device holder 1100. For instance, a tissue traction device 2100 may include a target-tissue-engaging segment 2112 configured to be engaged with the target tissue to which traction is to be applied. As described above, such target-tissue-engaging segment 2112 may be delivered with a tissue-engagement member 2200 already engaged therewith for use in engaging the target-tissue-engaging segment 2112 with the target tissue. Another portion of the tissue traction device 2100 may be engaged with a tissue traction device holder 1100 during delivery to the target tissue site as described above.

In accordance with various principles of the present disclosure, a tissue traction device, whether or not delivered with the assistance of a tissue traction device holder 1100, may include more than one portion engageable with tissue. Such portions of the tissue traction device may be referenced as tissue-engaging portions without intent to limit. It will be appreciated that the term engage (and other grammatical forms thereof) may be used interchangeably herein with other terms, such as couple, affix, anchor, secure, attach.

It will be appreciated that terms such as portion, area, section, segment, etc., may be used interchangeably herein without intent to limit, reference generally being made to a section as a general region, and a segment as a particular part, for the sake of convenient differentiation and without intent to limit. The various embodiments of tissue traction devices 2100, 3100, 4100, 5100, 6100, 7100, 8100, 9100 illustrated in FIG. 2, FIG. 3, FIG. 4, FIG. 5, FIG. 6, FIG. 7, FIG. 8, and FIG. 9, respectively, and formed in accordance with various principles of the present disclosure, include a peripheral section 2110, 3110, 4110, 5110, 6110, 7110, 8110, 9110 providing a plurality of grasping segments therealong, and one or more additional grasping segments 2120, 3120, 4120, 4122, 5120, 5122, 6120, 6122, 7120, 8120, 9120, 9122 which may be considered interior grasping segments (at least for the sake of convenience, such as to differentiate from description of the peripheral section, and without intent to limit) within the perimeter of the peripheral sections 2110, 3110, 4110, 5110, 6110, 7110, 8110, 9110. In some embodiments, a tissue traction device 2100, 3100, 4100, 5100, 6100, 7100, 8100, 9100 is generally elongated and may be considered generally to have an "end" engaged with target tissue, and another section engaged with tissue spaced apart from the target tissue (and optionally at another "end" of the elongated tissue traction device, or between the ends of the elongated tissue traction device) such as to anchor to such tissue (which may be referenced as "traction tissue" for the sake of convenient differentiation and without intent to limit) to apply traction to the target tissue. The end of the tissue traction device engaged with target tissue may be referenced herein (for the sake of convenience and without intent to limit) as a target-tissue-engaging end, and the end of the tissue traction device engaged with traction tissue (such as to anchor thereto to apply traction to the target tissue) may be referenced herein (for the sake of convenience and without intent to limit) as a traction-tissue-engaging end.

In some embodiments, the peripheral section 2110, 3110, 4110, 5110, 6110, 7110, 8110, 9110 of a respective tissue traction device 2100, 3100, 4100, 5100, 6100, 7100, 8100, 9100 formed in accordance with various principles of the present disclosure may be in the form of a loop, such as in the form of a circle or an ellipse, as illustrated respectively in FIG. 2, FIG. 3, FIG. 4, FIG. 5, FIG. 6, FIG. 7, FIG. 8, and FIG. 9. The peripheral section 2110, 3110, 4110, 5110, 6110, 7110, 8110, 9110 may be engaged with target tissue along a segment thereof, such as via a respective target-tissue-engaging segment 2112, 3112, 4112, 5112, 6112, 7112, 8112, 9112 along a respective first end 2111, 3111, 4111, 5111, 6111, 7111, 8111, 9111 thereof. If the peripheral section 2110, 3110, 4110, 5110, 6110, 7110, 8110, 9110 is in the form of an ellipse, the target-tissue-engaging segment 2112, 3112, 4112, 5112, 6112, 7112, 8112, 9112 may be positioned along a first focus of such ellipse. Another segment of the tissue traction device 2100, 3100, 4100, 5100, 6100, 7100, 8100, 9100 may be engaged with tissue spaced apart from the target tissue, such as to anchor such other segment to the other tissue. As such, the other tissue may be considered traction tissue, and the other segment may be considered a traction-tissue-engaging segment. Such engagement of the target-tissue-engaging segment 2112, 3112, 4112, 5112, 6112, 7112, 8112, 9112 of the tissue traction device 2100, 3100, 4100, 5100, 6100, 7100, 8100, 9100 with target tissue allows the tissue traction device 2100, 3100, 4100, 5100, 6100, 7100, 8100, 9100 to apply traction to the target tissue to which the target-tissue-engaging segment 2112, 3112, 4112, 5112, 6112, 7112, 8112, 9112 of the tissue traction device 2100, 3100, 4100, 5100, 6100, 7100, 8100, 9100 is engaged. Such traction-tissue-engaging segment may be along the peripheral section 2110, 3110, 4110, 5110, 6110, 7110, 8110, 9110, such as a peripheral traction-tissue-engaging segment 2114, 3114, 4114, 5114, 6114, 7114, 8114, 9114, or along a segment within the perimeter or interior (e.g., bounded by or otherwise radially inwardly) of the peripheral section 2110, 3110, 4110, 5110, 6110, 7110, 8110, 9110. In some embodiments, the target-tissue-engaging segment 2112, 3112, 4112, 5112, 6112, 7112, 8112, 9112 is along a second end 2113, 3113, 4113, 5113, 6113, 7113, 8113, 9113 of the peripheral section 2110, 3110, 4110, 5110, 6110, 7110, 8110, 9110, however other locations are within the scope and spirit of the present disclosure.

In accordance with various principles of the present disclosure, a tissue traction device has more than one traction-tissue-engaging segment to allow the medical professional to vary or adjust the force vector of traction applied to the target tissue by the tissue traction device. For instance, the tissue traction device which has been engaged with target tissue may be grasped along an initial, first traction-tissue-engaging segment and engaged (e.g., anchored) to traction tissue spaced apart from the target tissue. As the target tissue is resected or dissected or otherwise moved with respect to surrounding tissue at the target tissue site, traction applied by the tissue traction device may be reduced. To maintain a constant amount of traction on the target tissue, instead of moving the initial traction-tissue-engaging segment of the tissue traction device (as in prior art procedures), one or more grasping segments of the tissue traction device may be engaged simultaneously and/or sequentially with traction tissue spaced apart from the target tissue. More than one traction-tissue-engaging segment may be engaged with the same traction tissue to vary the force vector of traction applied to target tissue if the distances between the traction tissue and each of the traction-tissue-engaging segments are different. Alternatively or additionally, additional traction-tissue-engaging segments may be engaged with different traction tissue sites spaced from one another. Such other traction-tissue-engaging segments of the tissue traction device may be along the peripheral section of the tissue traction device and/or along an interior of the peripheral section or otherwise. For instance, each of the tissue traction devices 2100, 3100, 4100, 5100, 6100, 7100, 8100, 9100 illustrated in FIG. 2, FIG. 3, FIG. 4, FIG. 5, FIG. 6, FIG. 7, FIG. 8, and FIG. 9, respectively, includes a peripheral section 2110, 3110, 4110, 5110, 6110, 7110, 8110, 9110 with one or more additional grasping segments 2120, 3120, 4120, 4122, 5120, 5122, 6120, 6122, 7120, 8120, 9120, 9122 defined therein which may be used as target-tissue-engaging segments.

Figure 2:
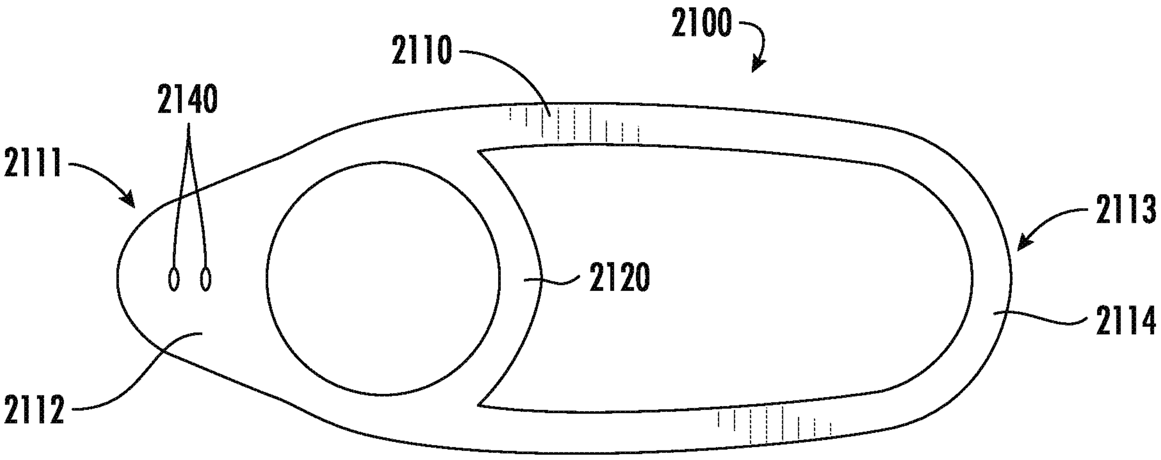
FIG. 2 illustrates a plan view of an example of an embodiment of a traction device formed in accordance with various principles of the present disclosure.
Figure 3:
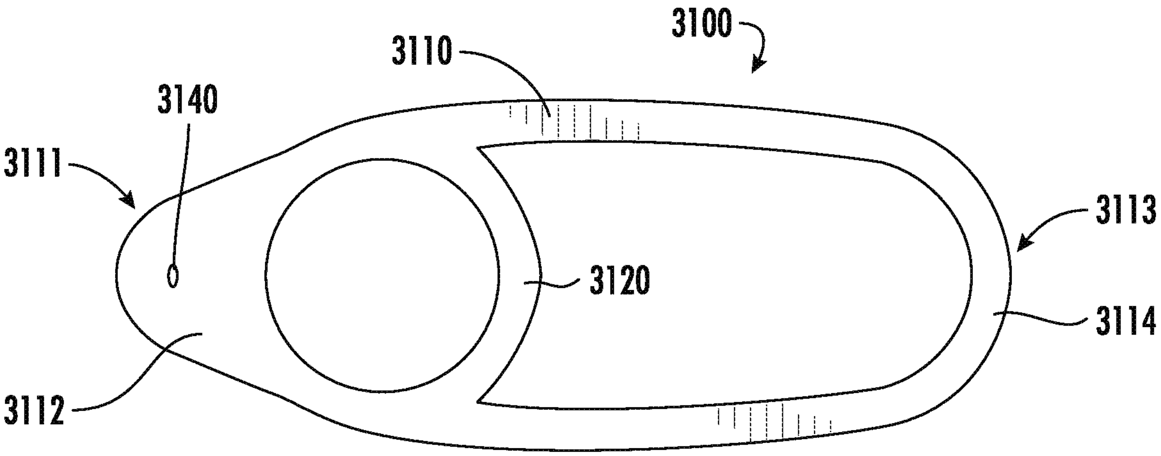
FIG. 3 illustrates a plan view of an example of an embodiment of a traction device formed in accordance with various principles of the present disclosure.

In the examples of embodiments of tissue traction devices 2100, 3100 respectively illustrated in FIG. 2 and FIG. 3, the additional grasping segments 2120, 3120 are in the form of a loop defined adjacent (e.g., about) the focus of the elliptically shaped peripheral section 2110, 3110 adjacent the target-tissue-engaging segment 2112, 3112. When an additional grasping segment 2120, 3120 is engaged (e.g., with the use of another tissue-engagement member) with traction tissue the same as or spaced apart from the target tissue to which the tissue traction device 2100, 3100 is initially engaged ("initial target tissue" at an "initial traction tissue site"), the tissue traction device 2100, 3100 may vary the force vector of traction applied to the target tissue and/or may adjust the angle of the traction applied to the target tissue. The additional grasping segments 2120, 3120 are illustrated as within the peripheral section 2110, 3110 of the tissue traction device 2100, 3100, although other locations are within the scope and spirit of the present disclosure.

Figure 4:
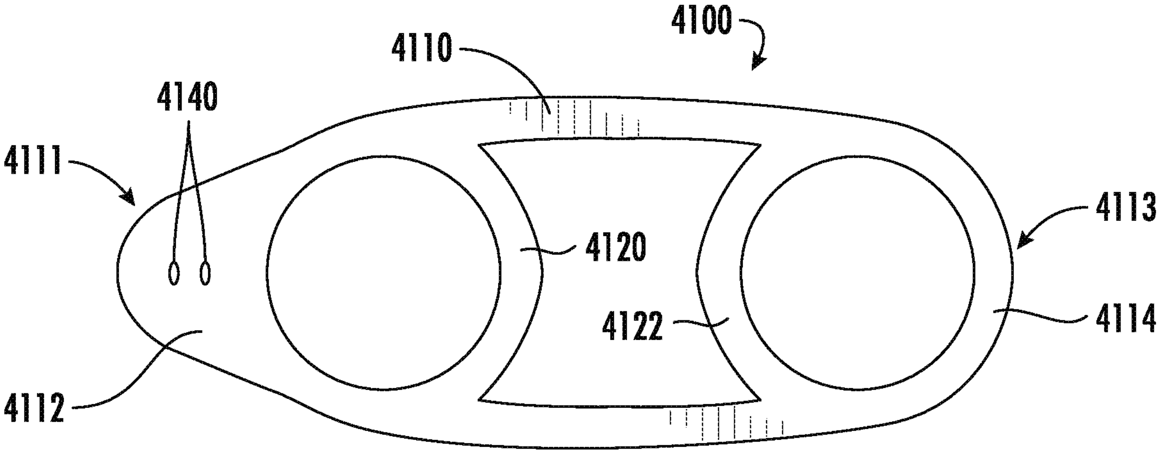
FIG. 4 illustrates a plan view of an example of an embodiment of a traction device formed in accordance with various principles of the present disclosure.
Figure 5:
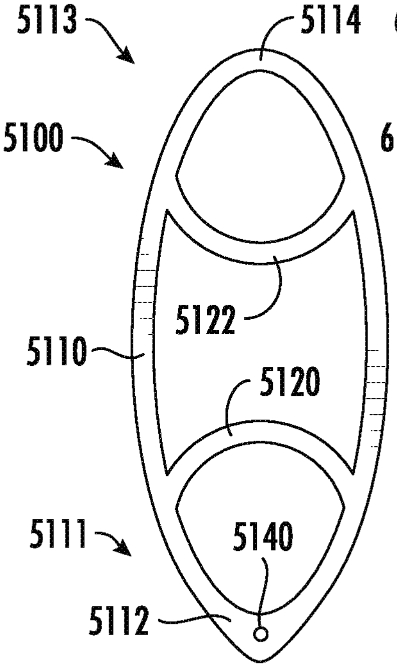
FIG. 5 illustrates a plan view of an example of an embodiment of a traction device formed in accordance with various principles of the present disclosure.

The examples of embodiments of tissue traction devices 4100, 5100 respectively illustrated in FIG. 4 and FIG. 5 also have additional grasping segments 4120, 5120 in the form of a loop defined adjacent (e.g., about) the focus of the elliptically shaped peripheral section 4110, 5110 adjacent the target-tissue-engaging segment 4112, 5112. Like the tissue traction devices 2100, 3100 of FIG. 2 and FIG. 3, respectively, with similar grasping segments 2120, 3120, engaging of an additional grasping segment 4120, 5120 of a tissue traction device 4100, 5100 with traction tissue, either the same as or spaced apart from the initial traction tissue, allows the respective tissue traction device 4100, 5100 to vary the force vector of traction applied to the target tissue. In addition, the tissue traction devices 4100, 5100 have additional grasping segments 4122, 5122 (which may also be in the form of a loop) spaced apart from the target-tissue-engaging segment 4112, 5112. For instance, the additional grasping segments 4122, 5122 may be defined adjacent (e.g., about) the other focus of the elliptically shaped peripheral section 4110, 5110. Such additional grasping segments 4122, 5122 allow further grasping and engagement of the respective tissue traction device 4100, 5100 to additional traction tissue sites to further vary the force vector of traction applied by the tissue traction device 4100, 5100 to the target tissue. The additional grasping segments 4122, 5122 are illustrated as within the peripheral section 4110,

5110 of the tissue traction device 4100, 5100, although other locations are within the scope and spirit of the present disclosure.

Figure 6:
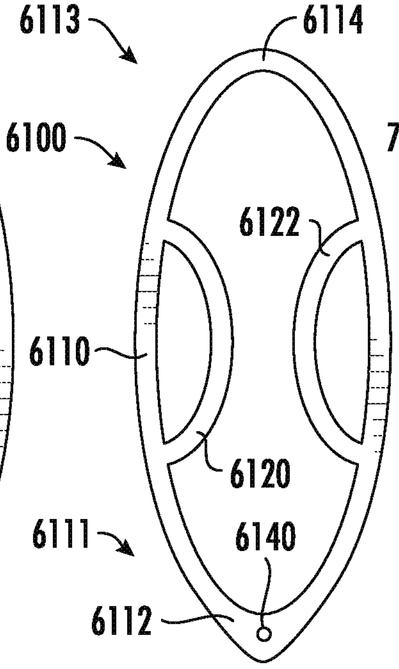
FIG. 6 illustrates a plan view of an example of an embodiment of a traction device formed in accordance with various principles of the present disclosure.

It will be appreciated that additional grasping segments may be positioned along other locations within or along the peripheral section of a tissue traction device. For instance, as illustrated in FIG. 6, a tissue traction device 6100 may have one or more grasping segments 6120, 6122 extending along the co-vertices of an elliptically-shaped peripheral section 6110 (along the longer sections of the ellipse extending generally in a direction of the major axis of the ellipse). The additional grasping segments 6120, 6122 are illustrated as within the peripheral section 6110 of the tissue traction device 6100, although other locations are within the scope and spirit of the present disclosure.

Figure 7:
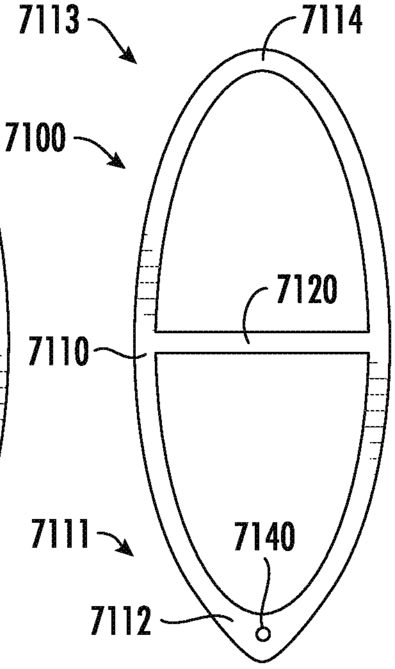
FIG. 7 illustrates a plan view of an example of an embodiment of a traction device formed in accordance with various principles of the present disclosure.

Moreover, it will be appreciated that additional grasping or traction segments may be in forms other than loops. In some embodiments, the additional traction segment extends transverse to the direction of extension of the tissue traction device between the target tissue and the traction tissue. For instance, as illustrated in FIG. 7, a tissue traction device 7100 may be formed in accordance with various principles of the present disclosure with an additional grasping segment 7120 extending transverse to the direction along which the tissue traction device 7100 extends between target tissue and traction tissue. For instance, in the example of an embodiment of a tissue traction device 7100 illustrated in FIG. 7, an additional grasping segment 7120 extends across the interior of the peripheral section 7110 of the tissue traction device 7100. Although the interior grasping segment 7120 of the tissue traction device 7100 is illustrated as generally straight and generally extending along the minor axis of a peripheral section 7110 in the form of an ellipse, tissue traction devices with interior grasping segments of other shapes and configurations and orientations within a peripheral section which may be, but is not limited to, an elliptical shape, are within the scope and spirit of the present disclosure.

Figure 8:
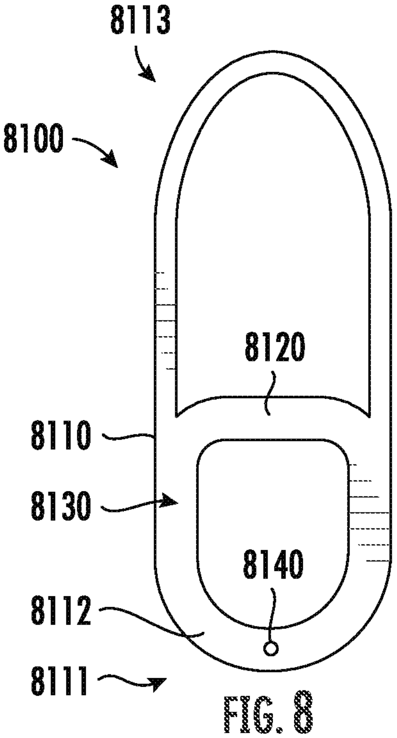
FIG. 8 illustrates a plan view of an example of an embodiment of a traction device formed in accordance with various principles of the present disclosure.
Figure 9:
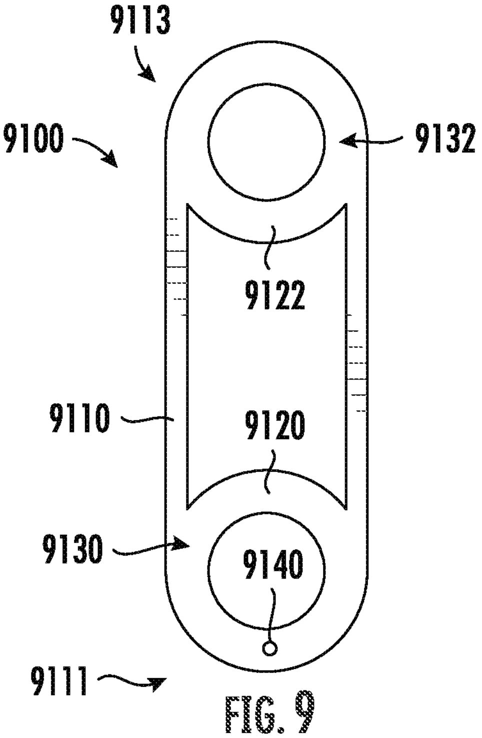
FIG. 9 illustrates a plan view of an example of an embodiment of a traction device formed in accordance with various principles of the present disclosure.

In accordance with various principles of the present disclosure, as may be appreciated with reference to the examples of embodiments of tissue traction devices 8100, 9100 illustrated in FIG. 8 and FIG. 9, respectively, the thickness of one or more sections of the tissue traction device formed in accordance with various principles of the present disclosure need not be the same. For instance, thicker areas or regions 8130, 9130, 9132 may be provided such as to increase resistance to elongation of such region, such as to increase traction applied by a segment along such section. In the example of an embodiment of a tissue traction device 8100 illustrated in FIG. 8, the target-tissue-engaging segment 8112 and an interior grasping segment 8120 extending across the interior of the peripheral section 8110 extend along a thicker region 8130 of the tissue traction device 8100. The interior grasping segment 8120 may extend along the minor axis of the peripheral section 8110 or slightly offset from the minor axis (e.g., as illustrated), and optionally may be curved, such as to form a loop configuration. In the example of an embodiment of a tissue traction device 9100 illustrated in FIG. 9, the target-tissue-engaging segment 9112 and two interior grasping segments 9120, 9122 extending across the interior of the peripheral section 9110 extend along a thicker region 9130 of the tissue traction device 9100. It will be appreciated that although the two interior grasping segments 9120, 9122 are illustrated as in the form of loops, such as generally along ends of an elongated peripheral section, other configurations are within the scope and spirit of the present disclosure, including, without limitation, generally straight segments.

In some embodiments, a tissue traction device formed in accordance with various principles of the present disclosure is configured to facilitate coupling the tissue traction device with a separately formed tissue-engagement member. The tissue traction device and/or the tissue-engagement member may be configured to keep the tissue traction device in place with respect to the tissue-engagement member. In some embodiments, the tissue traction device is provided with one or more assembly holes with which a tissue-engagement member may be engaged. For instance, at tissue-engagement member having a pair of grasper arms 2210 as illustrated in FIG. 1 may be engaged with a tissue traction device by introducing at least one of the grasper arms 2210 into an assembly hole in a tight fit, such as due to the friction and the elastomeric material of the tissue traction device contracting into the grasper arm 2210. Such fit ensures that the tissue traction device will stay in position during the procedure. The grasper arms 2210 may be shaped and/or configured (e.g., with a shoulder) to hold the tissue traction device in place with respect to the tissue-engagement member to resist inadvertent withdrawal of the grasper arm 2210 from the assembly hole. In the examples of embodiments of tissue traction device 2100, 4100 illustrated in FIG. 2 and FIG. 4, a pair of assembly holes 2140, 4140, respectively, is provided along a respective target-tissue-engaging segment 2112, 4112 of the tissue traction device 2100, 4100. Each grasper arm 2210 of a tissue-engagement member 2200 such as illustrated in FIG. 1 may be inserted into a respective hole 2140, 4140 of the pair of assembly holes 2140, 4140. It will be appreciated that the provision of at least one assembly hole can be modified to include only one assembly hole, simplifying the process of inserting only one grasper arm of a tissue-engagement member into an assembly hole of the tissue traction device to couple the tissue traction device with the tissue-engagement member. Such configuration and coupling may be advantageously used if back-loading the tissue traction device into a delivery device, and/or not using a tissue traction device holder 1100 as described above. The examples of embodiments of tissue traction devices 3100, 5100, 6100, 7100, 8100, 9100 are illustrated with only a single assembly hole 3140, 5140, 6140, 7140, 8140, 9140 adjacent the target-tissue-engaging segment 3112, 5112, 6112, 7112, 8112, 9112 of the tissue traction device 3100, 5100, 6100, 7100, 8100, 9100, respectively. It will be appreciated that other configurations are within the scope and spirit of the present disclosure. For instance, if it is desirable to pre-load an additional tissue-engagement member engaged with the tissue traction device, additional assembly holes may be provided for such additional tissue-engagement member.

As described above, a segment of a tissue traction device formed in accordance with various principles of the present disclosure may be engaged with an initial tissue site (referenced as target tissue for the sake of simplicity and without intent to limit), such as with a tissue-engagement member (optionally pre-loaded on the tissue traction device), and then another segment of the tissue traction device may be engaged with another region of tissue (referenced herein as traction tissue and/or a traction tissue site for the sake of convenience and without intent to limit) to apply traction to the target tissue via the tissue traction device. The target tissue site may be within a body passage or lumen (such as, without limitation, a gastrointestinal tract such as the small or large intestine), with the traction tissue along a wall of the body passage or lumen opposite the target tissue. Of course, it will be appreciated that devices, systems, and methods in in accordance with various principles of the present disclosure may be used in connection with other anatomical regions and/or structures.

An example of a use of an example of an embodiment of a tissue traction device 2100 in accordance with various principles of the present disclosure is illustrated in FIG. 10 and FIG. 11. The example of an embodiment of a tissue traction device 2100 is illustrated in FIG. 10 engaged with target tissue TA at a target tissue site TS with the use of a tissue-engagement member 2200. More particularly, a grasper arm 2210 of the tissue-engagement member 2200 is inserted through an assembly hole 2140 (see FIG. 2) adjacent a target-tissue-engaging segment 2112 to couple the tissue traction device 2100 to the target tissue TA. A peripheral traction-tissue-engaging segment 2114, along a peripheral section 2110 of the tissue traction device 2100 and spaced apart from the target-tissue-engaging segment 2112, is engaged with traction tissue TR1 spaced apart from the target tissue TA with the use of another tissue-engagement member 2202. The tissue traction device 2100 may thereby apply traction to the target tissue TA. An endoscope 1300 is illustrated as delivering a tissue manipulating device 1400 to the target tissue site TS to manipulate the target tissue TA to which traction is being applied by the tissue traction device 2100. In the illustrated example, the tissue-manipulating device 1400 separates the target tissue TA from the surrounding tissue at the target tissue site TS. As the target tissue TA is separated from surrounding tissue, the target tissue TA lifts away from surrounding tissue at the target tissue site TS, relieving some of the traction exerted by the tissue traction device 2100.

As illustrated in FIG. 11, to increase traction on the target tissue TA, an interior grasping segment 2120 is engaged, such as with the use of an additional tissue-engagement member 2204, with traction tissue TR2 spaced apart from the traction tissue TR1 to which the traction-tissue-engaging segment 2114 has been engaged. As may be appreciated, the additional traction on the target tissue TA causes the target tissue TA to lift further away from the surrounding tissue to allow the procedure being performed with the tissue-manipulating device 1400 to be continued without interference by the target tissue TA. It will be appreciated that if the distance between the interior grasping segment 2120 and the target tissue TA is shorter than the distance between the traction-tissue-engaging segment 2114 and the target tissue TA, engagement of the interior grasping segment 2120 with the same traction tissue T1 to which the traction-tissue-engaging segment 2114 is engaged may still vary the force vector of traction applied by the tissue traction device 2100 to the target tissue TA.

Although the tissue traction device 2100 illustrated in FIG. 10 and FIG. 11 appears similar to the tissue traction device 2100 illustrated in FIG. 2, it will be appreciated that other configurations of tissue traction devices (including, but not limited to, the tissue traction devices 3100, 4100, 5100, 6100, 7100, 8100, 9100 illustrated in FIG. 3, FIG. 4, FIG. 5, FIG. 6, FIG. 7, FIG. 8, and FIG. 9, respectively) may be used as described.

It will be appreciated that the above-described examples of embodiments of tissue traction devices 2100, 3100, 4100, 5100, 6100, 7100, 8100, 9100 illustrate examples of various principles of the present disclosure, the present disclosure not being limited by such examples. Various structures and features of the embodiments described herein and illustrated in the figures have several separate and independent unique benefits. Therefore, the various structures and features described herein need not all be present in order to achieve at least some of the desired characteristics and/or benefits described herein. Moreover, the various features described herein may be used singly or in any combination. It will be appreciated that various features described with respect to one embodiment may be applied to another embodiment, whether or not explicitly indicated. Thus, it should be understood that one or more of the features described with reference to one embodiment can be combined with one or more of the features of any of the other embodiments described herein. That is, any of the features described herein can be mixed and matched to create hybrid designs, and such hybrid designs are within the scope of the present disclosure. Therefore, the present invention is not limited to only the embodiments specifically described herein. The above descriptions are of illustrative examples of embodiments only, and are not intended as limiting the broader aspects of the present disclosure.

It should be appreciated that surgical dissection or resection of a target tissue as discussed herein typically includes removal of a portion of the surrounding healthy tissue along the target tissue margin to ensure complete removal and to minimize the potential for metastasis of left-behind or dislodged target tissue cells to other body locations. The target tissue may be within a target tissue area in the body, such as the gastrointestinal system. Terms such target tissue area, target tissue site, target area of tissue, target area, target site, target treatment area, treatment area, target treatment site, treatment site, etc., may be used interchangeably herein, without intent to limit, to refer to an area or region of tissue on which a procedure is to be performed or which is to be treated or otherwise operated on or affected by the devices and/or systems and/or methods disclosed herein, including areas or regions extending outwardly from or around or surrounding the target tissue (specific tissue in the target tissue area). The various principles of the present disclosure may, of course, be more widely applicable, such as beyond tissue resection/dissection.

It will be appreciated that other uses of a tissue-engagement member formed in accordance with various principles of the present disclosure are within the scope and spirit of the present disclosure. Although embodiments of the present disclosure may be described with specific reference to medical devices and systems and procedures for treating the gastrointestinal system, it should be appreciated that such medical devices and methods may be used to treat tissues of the abdominal cavity, digestive system, urinary tract, reproductive tract, respiratory system, cardiovascular system, circulatory system, and the like.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, engaged, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements, components, features, regions, integers, steps, operations, etc. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A tissue traction device comprising:

a peripheral section defining a perimeter of said tissue traction device and having an elliptical shape and at least one grasping segment engageable with tissue; and at least one additional grasping segment extending within the perimeter of said peripheral section and engageable with tissue;

wherein:

said grasping segments define a target-tissue-engaging segment engageable with a target tissue, a first traction-tissue-engaging segment engageable with traction tissue spaced apart from the target tissue to apply traction to the target tissue, and a second traction-tissue-engaging segment engageable with traction tissue to vary the force vector of traction applied to the target tissue by the first traction-tissue-engaging segment;

said target-tissue-engaging segment is defined along a first focus of said elliptical peripheral section;

said first traction-tissue-engaging segment is defined along a second focus of said elliptical peripheral section; and said second traction-tissue-engaging segment is a loop extending about the first focus of said elliptical peripheral section.

2. The tissue traction device of claim 1, wherein the distance between the second traction-tissue-engaging segment and the target tissue is shorter than the distance between the first traction-tissue-engaging segment and the target tissue.

3. The tissue traction device of claim 2, wherein the first traction-tissue-engaging segment and the second traction-tissue-engaging segment are configured to be engaged to traction tissue at the same location.

4. The tissue traction device of claim 2, wherein the first traction-tissue-engaging segment is configured to be engaged to traction tissue at a first location, and the second traction-tissue-engaging segment is configured to be engaged to traction tissue at a second location spaced apart from the first location.

5. The tissue traction device of claim 1, wherein the first traction-tissue-engaging segment is configured to be engaged to traction tissue at a first location, and the second traction-tissue-engaging segment is configured to be engaged to traction tissue at a second location spaced apart from the first location to vary the force vector of traction applied to the target tissue.

6. The tissue traction device of claim 1, wherein one or more assembly holes are defined through said target tissue-engaging segment.

7. The tissue traction device of claim 6, further comprising a tissue engagement member with at least one grasper arm extendable through at least one of the one or more assembly holes.

8. The tissue traction device of claim 1, wherein at least one of said first traction-tissue-engaging segment or said second traction-tissue-engaging segment is in the form of a loop.

9. The tissue traction device of claim 1, wherein at least one of said grasping segments extends transverse to the direction in which said tissue traction device extends between the target tissue and the traction tissue.

10. The tissue traction device of claim 1, wherein at least one of said grasping segments has a thickness different from another grasping segment of said tissue traction device.

11. The tissue traction device of claim 1, wherein said tissue traction device is formed of an elastic material.

12. A delivery system for a tissue traction system, said delivery system comprising:

a tissue traction device defining a peripheral section in the form of an elliptical loop defining at least one target-tissue-engaging segment defined along a first focus of said elliptical loop, at least one traction-tissue-engaging segment spaced apart from said target-tissue-engaging segment and defined along a second focus of said elliptical loop, and at least one grasping segment in the form of a loop extending about the first focus of said elliptical loop; and a tissue traction device holder engageable with said tissue traction device to maintain said target-tissue-engaging segment spaced apart from said traction-tissue-engaging segment.

13. The delivery system of claim 12, wherein the tissue traction device further comprises at least one additional grasping segment defined along said peripheral section or extending within a perimeter defined by said peripheral section.

14. The delivery system of claim 12, wherein said tissue traction system further includes a tissue-engagement member engaged with said target-tissue-engaging segment of said tissue traction device.

15. The delivery system of claim 14, further comprising a tissue-engagement member delivery device extending within said tissue traction device holder and maintaining said tissue-engagement member and said target-tissue-engaging segment of said tissue traction device engaged therewith spaced apart from a portion of said tissue traction device engaged with said tissue traction device holder.

16. A method of applying traction to a target tissue, said method comprising:

engaging a target-tissue-engaging segment defined along a first focus of an elliptical tissue traction device with target tissue;

engaging a first traction-tissue-engaging segment defined along a second focus of the elliptical tissue traction device with traction tissue spaced apart from the target tissue to apply traction to the target tissue; and engaging a second traction-tissue-engaging segment in the form of a loop extending about the first focus of the elliptical tissue traction device with traction tissue spaced apart from the target tissue to vary the force vector of the traction applied to the target tissue.

17. The method of claim 16, wherein the tissue traction device comprises a peripheral section defining a perimeter of the tissue traction device and at least one traction-tissue-engaging segment extending within the perimeter of the peripheral section, said method further comprising:

engaging a target-tissue-engaging segment along the peripheral section of the tissue traction device with target tissue;

engaging a first traction-tissue-engaging segment of the tissue traction device with traction tissue spaced apart from the target tissue to apply traction to the target tissue; and engaging a second traction-tissue-engaging segment of the tissue traction device extending within the perimeter of the peripheral section of the tissue traction device with traction tissue spaced apart from the target tissue to vary the force vector of the traction applied to the target tissue.

18. The method of claim 16, wherein the distance between the second traction-tissue-engaging segment and the target tissue is shorter than the distance between the first traction-tissue-engaging segment and the target tissue, said method further comprising engaging the first traction-tissue-engaging segment and the second traction-tissue-engaging segment to traction tissue at the same location.

19. The method of claim 16, wherein engaging the second traction-tissue-engaging segment to traction tissue comprises engaging the second traction-tissue-engaging segment to traction tissue spaced apart from traction tissue to which the first traction-tissue-engaging segment is engaged.

20. The method of claim 16, further comprising delivering the tissue traction device to the target tissue with a tissue traction device holder maintaining the target-tissue-engaging segment of the tissue traction device apart from the first traction-tissue-engaging segment of the tissue traction device.

* * * * *